United States Patent
McNames et al.

(10) Patent No.: US 9,301,712 B2
(45) Date of Patent: Apr. 5, 2016

(54) METHOD AND APPARATUS FOR CONTINUOUS MEASUREMENT OF MOTOR SYMPTOMS IN PARKINSON'S DISEASE AND ESSENTIAL TREMOR WITH WEARABLE SENSORS

(75) Inventors: James McNames, Portland, OR (US); Pedro Mateo Riobo Aboy, Beaverton, OR (US); Andrew Greenberg, Portland, OR (US)

(73) Assignees: PORTLAND STATE UNIVERSITY, Portland, OR (US); APDM, INC., Portland, OR (US)

( * ) Notice: Subject to any disclaimer, the term of this patent is extended or adjusted under 35 U.S.C. 154(b) by 330 days.

(21) Appl. No.: 12/511,038

(22) Filed: Jul. 28, 2009

(65) Prior Publication Data
US 2010/0030119 A1 Feb. 4, 2010

Related U.S. Application Data

(60) Provisional application No. 61/084,336, filed on Jul. 29, 2008.

(51) Int. Cl.
*A61B 5/11* (2006.01)
*A61B 5/00* (2006.01)

(52) U.S. Cl.
CPC ............ *A61B 5/1101* (2013.01); *A61B 5/4082* (2013.01)

(58) Field of Classification Search
CPC ............................ A61B 5/1101; A61B 5/4082
USPC .......................................................... 600/595
See application file for complete search history.

(56) References Cited

U.S. PATENT DOCUMENTS

| | | | |
|---|---|---|---|
| 4,117,834 A | 10/1978 | Mc Partland | |
| 4,306,291 A | 12/1981 | Zilm | |
| 4,353,375 A | 10/1982 | Colburn | |
| 5,293,879 A | 3/1994 | Vonk | |
| 5,562,104 A | 10/1996 | Hochberg | |
| 5,573,011 A * | 11/1996 | Felsing | 600/595 |
| 5,645,077 A | 7/1997 | Foxlin | |
| 5,744,953 A | 4/1998 | Hansen | |
| 6,691,074 B1 | 2/2004 | Moriya | |
| 7,089,148 B1 | 8/2006 | Bachmann | |
| 7,141,026 B2 | 11/2006 | Aminian | |
| 7,210,240 B2 | 5/2007 | Townsend | |
| 7,395,181 B2 | 7/2008 | Foxlin | |
| D614,979 S | 5/2010 | McNames | |
| 2004/0015103 A1 | 1/2004 | Aminian | |
| 2005/0010139 A1 | 1/2005 | Aminian | |
| 2005/0234309 A1 | 10/2005 | Klapper | |
| 2006/0241510 A1 * | 10/2006 | Halperin et al. | 600/534 |
| 2007/0032748 A1 | 2/2007 | Mcneil | |
| 2007/0123754 A1 * | 5/2007 | Cuddihy et al. | 600/595 |
| 2007/0249968 A1 | 10/2007 | Miesel | |

(Continued)

*Primary Examiner* — Linda Dvorak
*Assistant Examiner* — Emily Lloyd
(74) *Attorney, Agent, or Firm* — Mateo Aboy; Aboy & Associates PC

(57) ABSTRACT

Disclosed embodiments include an apparatus for generating a plurality of movement impairment indices from one or more kinematic signals to characterize movement disorders. Additionally we disclose methods for generating a plurality of movement impairment indices from one or more kinematic signals obtained from one or more kinematic sensors, said methods implemented in a digital computer with one or more processors in order to characterize movement disorders based on spectral analysis, regularity metrics, and time-frequency analysis.

14 Claims, 5 Drawing Sheets

(56) References Cited

U.S. PATENT DOCUMENTS

| | | |
|---|---|---|
| 2007/0255118 A1 | 11/2007 | Miesel |
| 2008/0053253 A1 | 3/2008 | Moore |
| 2008/0284650 A1 | 11/2008 | Macintosh |
| 2008/0285805 A1 | 11/2008 | Luinge |
| 2009/0131495 A1* | 5/2009 | Kim et al. .................. 514/397 |
| 2009/0281830 A1 | 11/2009 | McNames |
| 2010/0030119 A1 | 2/2010 | McNames |
| 2010/0076348 A1 | 3/2010 | McNames |
| 2010/0145236 A1 | 6/2010 | Greenberg |

* cited by examiner

METHOD AND APPARATUS FOR CONTINUOUS MEASUREMENT OF MOTOR SYMPTOMS IN PARKINSON'S DISEASE AND ESSENTIAL TREMOR WITH WEARABLE SENSORS

CROSS-REFERENCE TO RELATED APPLICATIONS

This application claims the benefit of U.S. Provisional Application No. 61/084,336, filed on Jul. 29, 2008 by the present inventors, which is incorporated herein by reference.

FEDERALLY SPONSORED RESEARCH

Not Applicable

SEQUENCE LISTING OR PROGRAM

Not Applicable

BACKGROUND

1. Technical Field

This invention relates to methods and apparatus for continuous measurement of motor symptoms in movement disorders. Specifically, it relates to methods and devices for continuous measurement of motor symptoms in movement disorders including Parkinson's disease and essential tremor by means of wearable kinematic sensors and signal processing analysis methods to determine impairment indices.

2. Related Art

Parkinson's disease (PD) is the second most common neurodegenerative disease and the most common serious movement disorder. It afflicts approximately 1 million in the US alone costing the economy over $25 billion annually. Levodopa is the most potent antiparkinson drug and is the primary therapy for most patients. However, continual use of levodopa over time causes fluctuations in bradykinesia (slowness of movement), tremor, and dyskinesia (uncoordinated writhing movements) and has variable effects on gait and posture. Accurate assessment of Parkinsonian motor impairments is crucial for optimizing therapy in clinical practice and for determining efficacy of new therapies in clinical trials. Subjective clinical rating scales such as the Unified Parkinson's Disease Rating Scale (UPDRS) are the most widely accepted standard for motor assessment. Objective static devices have also been developed to assess impairment more accurately and consistently. However, the value of both subjective and objective forms of static motor assessment may be limited in certain situations because each patient's motor state varies continuously throughout the day.

In recent years, large advances have been made in micro-electro-mechanical systems (MEMS) and inertial sensors, in particular. It is now possible to record body movements for hours with small, low-power, wearable sensors that include accelerometers, gyroscopes, goniometers, and magnetometers. However, the feasibility of using these sensors to quantify motor deficits associated with PD remains unknown.

Current inertial monitoring systems can be divided into three categories: computer-tethered, unit-tethered, and untethered. Computer-tethered devices connect the sensor directly to a computer. Unit-tethered systems connect the sensors to a central recording unit that is typically worn around the waist.

The only wireless untethered systems reported in the literature are "activity monitors," which measure the coarse degree of activity at intervals of 1-60 s, typically with a wrist-worn device that contains a single-axis accelerometer. These devices are sometimes called actigraphs or actigraphers.

Most prior work on continuous monitoring of PD has used unit-tethered systems during in-patient studies. Most of these studies have used accelerometers, but some have used gyroscopes.

Currently there are no systems or detailed automatic methods designed to obtain impairment indices for Parkinson's disease or essential tremor in continuous monitoring settings in order to help guide therapy and or continuously monitor the symptoms of movement disorders.

SUMMARY

Disclosed embodiments include an apparatus for generating a plurality of movement impairment indices from one or more kinematic signals to characterize movement disorders, comprising (a) one or more kinematic sensors to collect said kinematic signals; (b) means for processing said kinematic signals to reject artifacts and noise resulting in enhanced kinematic signals; (c) means finding a measure of power spectral density of said enhanced kinematic signals. Disclosed embodiments include a method for generating a plurality of movement impairment indices from one or more kinematic signals obtained from one or more kinematic sensors, said method implemented in a digital computer with one or more processors in order to characterize movement disorders, comprising (a) collecting said kinematic signals from said kinematic sensors; (b) processing said kinematic signals to reject artifacts and noise resulting in enhanced kinematic signals; (c) finding a measure of power spectral density of said enhanced kinematic signals; and (e) calculating a plurality of impairment indices from said measure of power spectral density.

BRIEF DESCRIPTION OF THE DRAWINGS

Disclosed embodiments are illustrated by way of example, and not by way of limitation, in the figures of the accompanying drawings.

DETAILED DESCRIPTION

According to one embodiment, estimation of motor symptoms in patients with Parkinson's disease or essential tremor is accomplished by processing signal data collected from wearable sensors. Signals are collected from a plurality of kinematic sensors including accelerometers, gyroscopes, and magnetometers.

Figure 1:
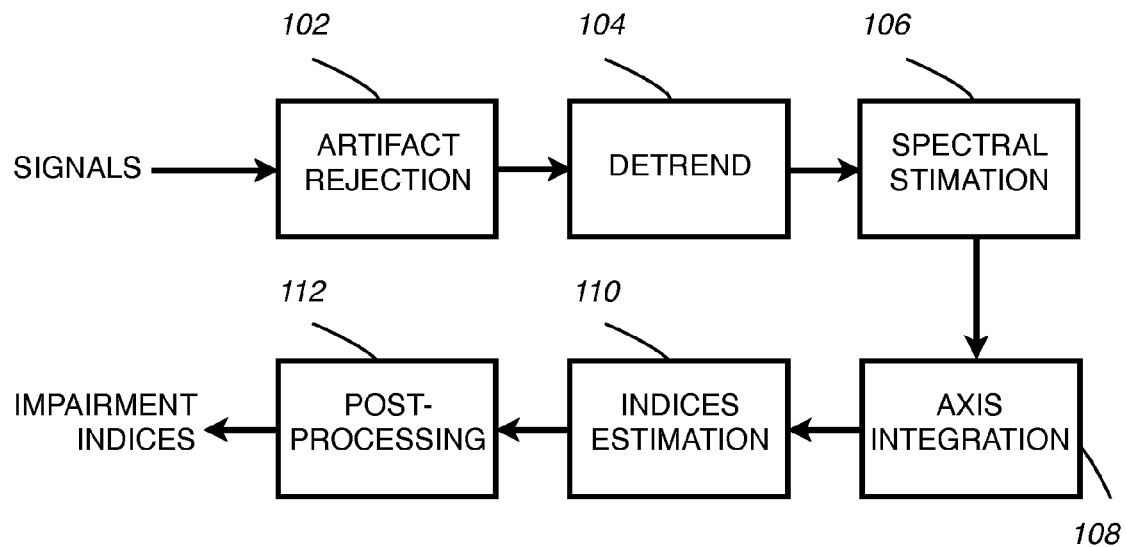
FIG. 1 illustrates a block diagram of a method for generating impairment indices from data collected from kinematic sensors including inertial sensors such as accelerometers and gyroscopes according to a embodiment.

FIG. 1 illustrates a block diagram of a method for generating impairment indices from data collected from kinematic sensors including inertial sensors such as accelerometers and gyroscopes according to one embodiment. According to one embodiment, each sensor may be used at multiple locations or orientations such as the wrists, ankles, trunk, and limbs. In this embodiment, the signals acquired from the sensors go through a artifact rejection block 102 and are detrended 104 to remove low frequency components. Then spectral estimation is performed 106 and an axis integration module 108 combines the spectral information from each of the three axes. The output of 108 is used to calculate indices of motor impairment 110 including tremor, dyskinesia, and bradykinesia. A postprocessing 112 is used to remove outliners and smooth the impairment estimates generated in 110. In its most basic form, this embodiment comprises a sequence of method steps designed to analyze signals obtained from a plurality of inertial wearable sensors and generates impairment indices for movement disorders such as Parkinson's disease and essential tremor in order to help guide therapy, assist in the diagnosis, and continuously monitor symptoms. The method steps may be incorporated in firmware or software as part of devices, apparatus, and systems for continuous monitoring of movement disorders for the purposes of monitoring, diagnosis, and treatment optimization.

According to a more specific embodiment illustrated by way of example, and not by way of limitation, the processing consist of the following steps:

Reduce artifacts in each signal using a plurality of digital signal processing and statistical signal processing methods to remove artifacts and limit the signal to a range consistent with the known possible range of movement angular velocity or acceleration.

If a MEMS gyroscope is used, the signal may be detrended to eliminate the effects of sensor drift. This can be achieved with a highpass filter or similar well known technique.

The spectral power in different frequency bands corresponding to specific impairments is then estimated for each signal. In the disclosed embodiment this is performed by applying bandpass filters followed by computing the squared value of the filter outputs $$y_i(n) = |x_i(n) * h(n)|^2 \qquad (1)$$

where $x_i(n)$ is the ith channel of the sensor, $h(n)$ is the impulse response of the bandpass filter, and $y_i(n)$ is the output of this stage. Alternatively, the spectral power could be calculated using well known nonparametric or parametric spectral estimation techniques such as the periodogram, modified periodogram, Barletts's method, Welch's method, Blackman-Tukey's method, autoregressive spectrum estimation, moving average spectrum estimation, and autoregressive moving average spectrum estimation. Additionally, these techniques can be used to generate time-frequency plots of power spectral density such as spectrograms. Similarly, wavelets can be used in this step and their corresponding time-frequency map, the scalogram.

According to this embodiment and without limitation, the bandlimited signal powers from each of the three axes may then be combined as follows $$p(n) = \sqrt{\sum_{i=1}^{3} y_i^2(n)} \qquad (2)$$

This signal can be understood as the total magnitude of acceleration (accelerometers) or rotational rate (gyroscopes) within a given frequency band.

The motor symptoms of PD can then be estimated as a function of these bandlimited power magnitudes. According to one embodiment and without limitation, dyskinesia can be represented as the total power magnitude in the frequency range of 1-4 Hz. Tremor can be represented as the percentage of total power magnitude in the frequency range of 4-8 Hz relative to the total power in the frequency range of 1-8 Hz. Bradykinesia can be represented as the inverse of the total power magnitude over the frequency range of 0.4-15 Hz.

Once the instantaneous metrics of the various forms of motor impairment are calculated, they are smoothed with a lowpass filter or other smoothing technique to reduce variability over time and more clearly display the degree of impairment in a plot.

Figure 2:
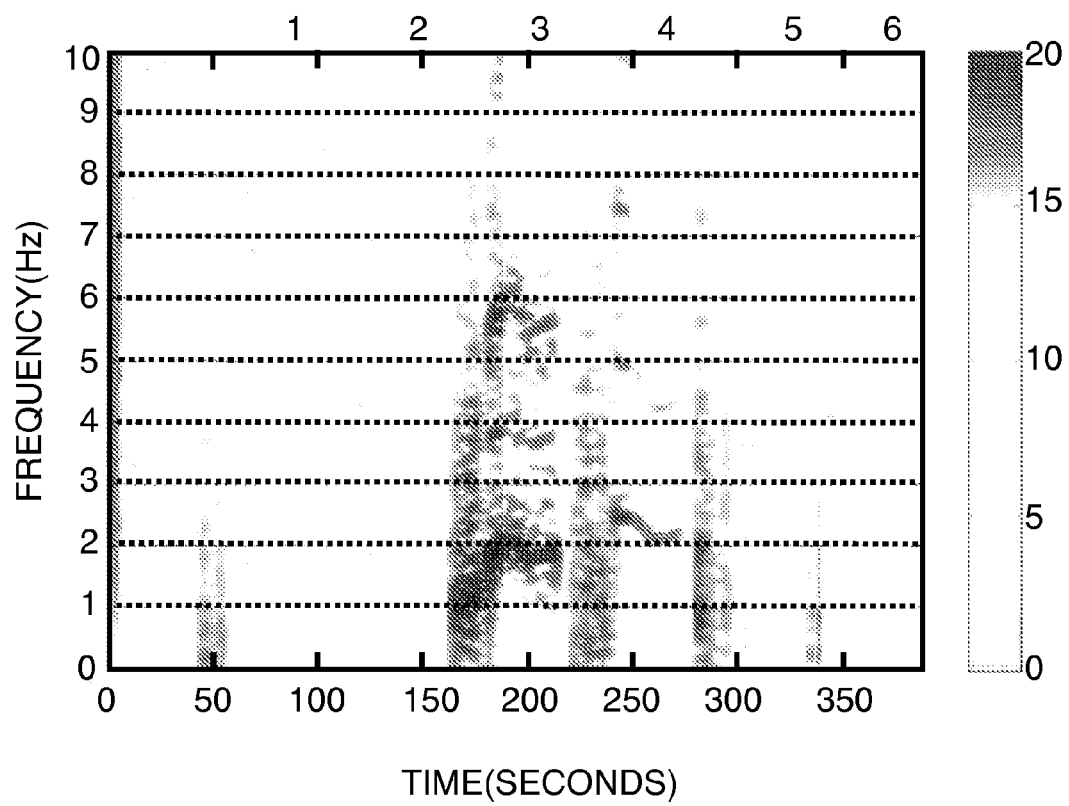
FIG. 2 illustrates an example of a time-frequency analysis (spectrogram) results obtained according to a disclosed embodiment for a control subject.
Figure 3:
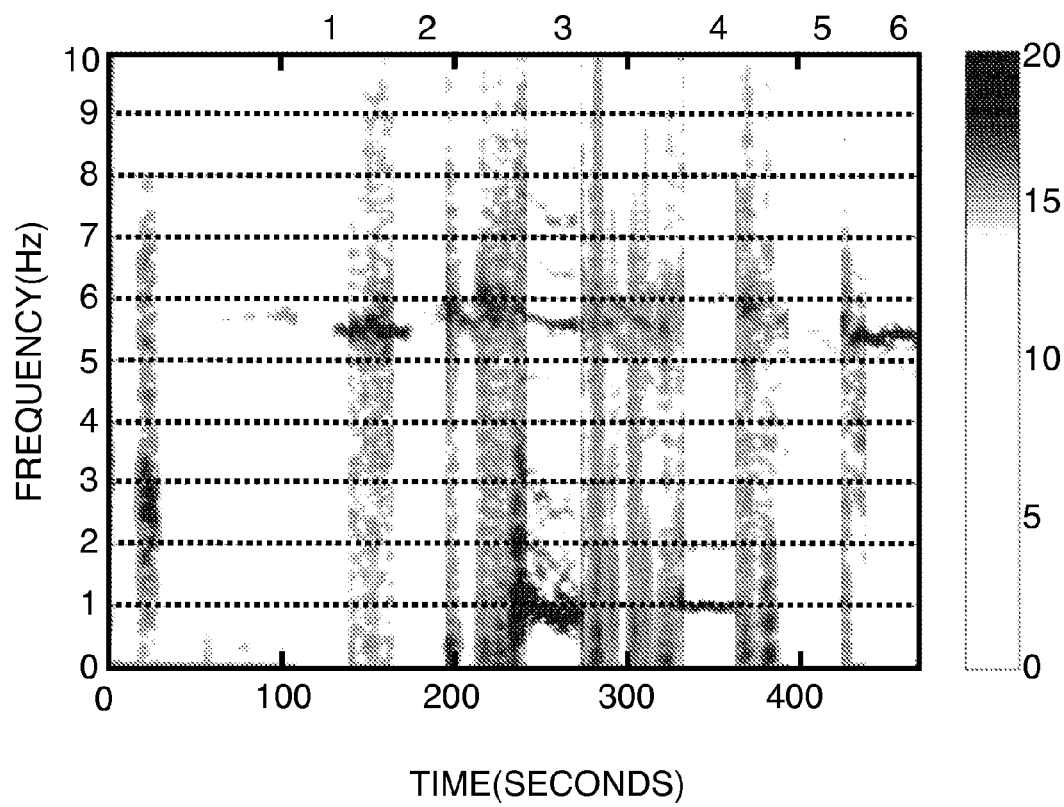
FIG. 3 illustrates an example of a time-frequency analysis (spectrogram) results obtained according to a disclosed embodiment for a patient with tremor.
Figure 4:
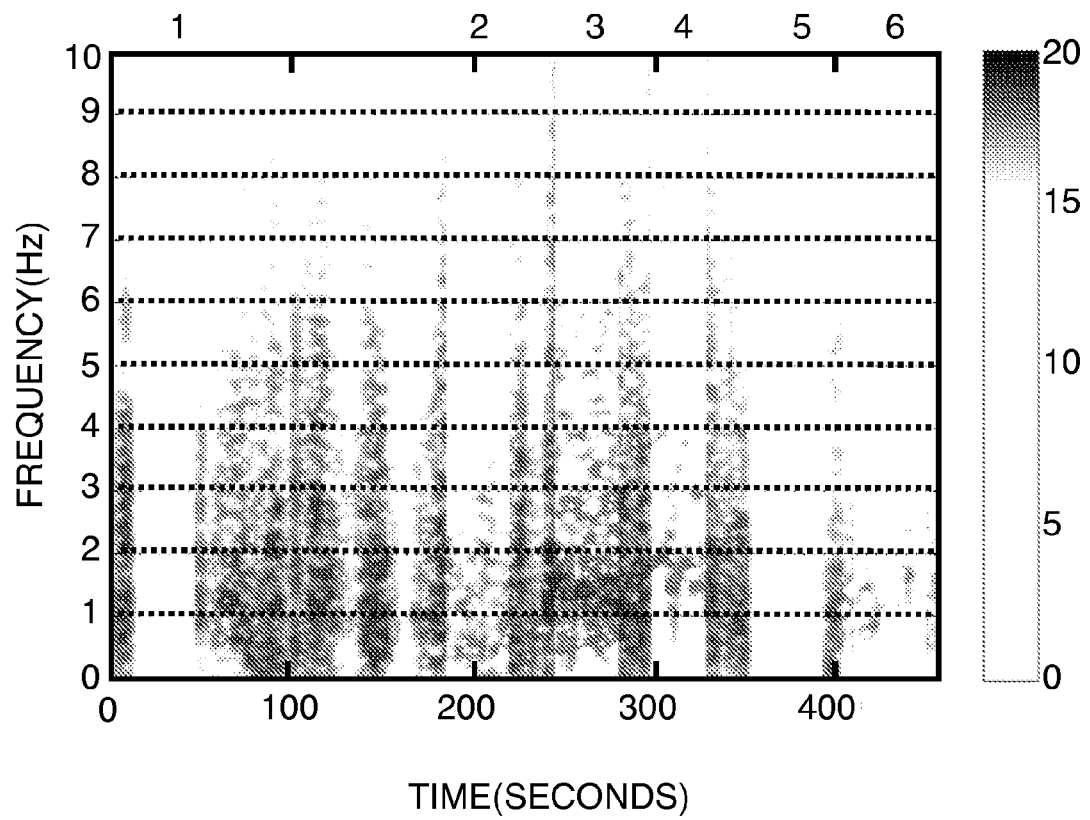
FIG. 4 illustrates an example of a time-frequency analysis (spectrogram) results obtained according to a disclosed embodiment for a patient with dyskinesia.
Figure 5:
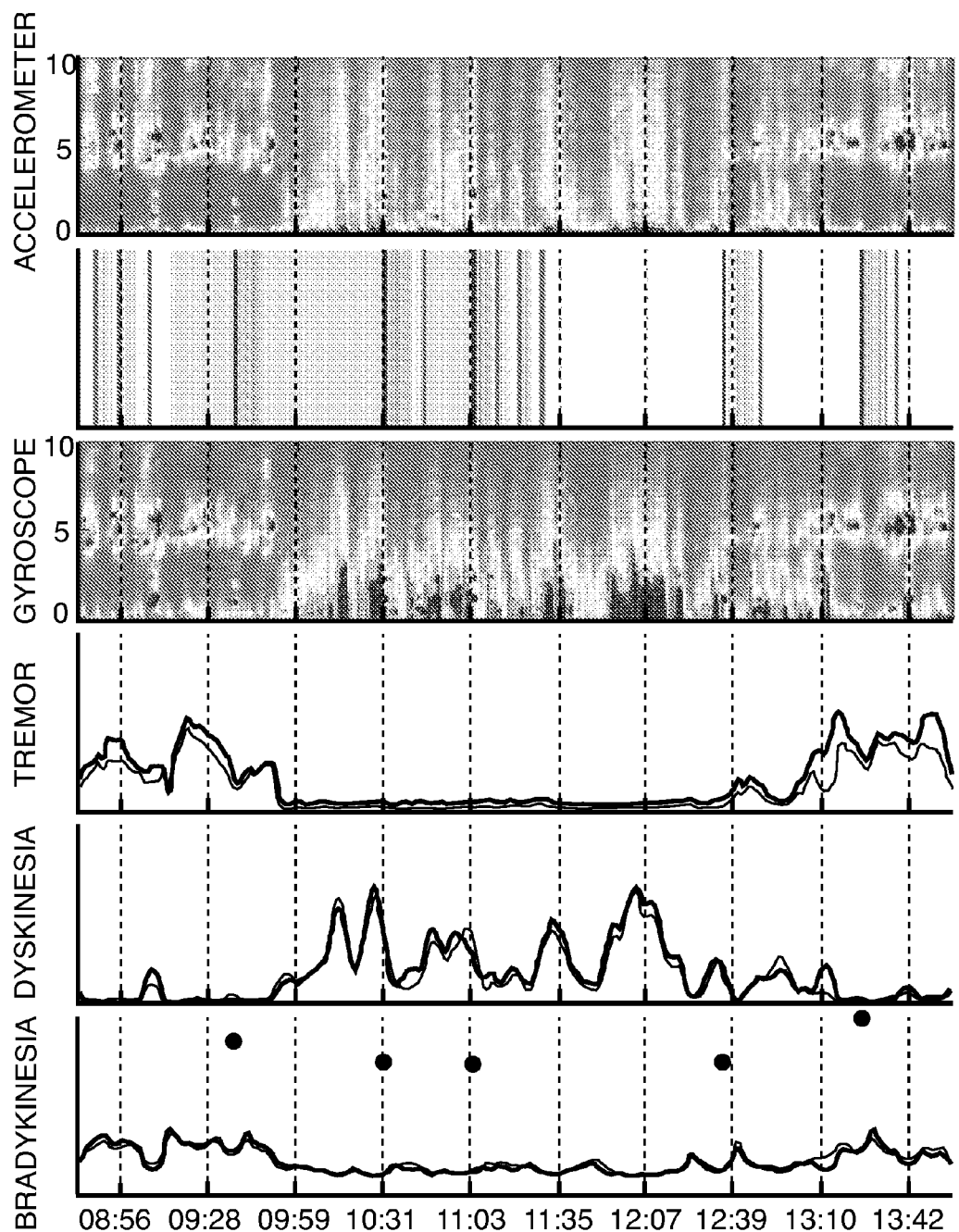
FIG. 5 illustrates an example of a resulting plot obtained according to a disclosed embodiment including the spectrogram of the accelerometer data, annotated activities, spectrogram of the gyroscope data, and the output impairment indices of tremor, dyskinesia, and bradykinesia.

FIG. 2 illustrates an example of a time-frequency analysis (spectrogram) results obtained according to a disclosed embodiment for a control subject. FIG. 3 illustrates an example of a time-frequency analysis (spectrogram) results obtained according to a disclosed embodiment for a patient with tremor. FIG. 4 illustrates an example of a time-frequency analysis (spectrogram) results obtained according to a disclosed embodiment for a patient with dyskinesia. FIG. 5 illustrates an example of a resulting plot obtained according to a disclosed embodiment including the spectrogram of the accelerometer data, annotated activities, spectrogram of the gyroscope data, and the output impairment indices of tremor, dyskinesia, and bradykinesia.

The description of the embodiment above does not represent a step-by-step sequence. The operations and methods detailed may be applied following a different order or techniques resulting in substantially equivalent results. The method can be implemented in hardware and firmware to make a movement disorders monitor and in software as part of a program to analyze signals from wearable sensors to monitor the motor symptoms of Parkinson's disease.

According to one embodiment, time-frequency analysis (spectrograms or scalograms) are performed for each channel of kinematic data. The power spectral densities can be estimated with a modified periodogram or other spectral analysis methods. Based on the orthogonality of the accelerometer and gyroscope channels, the spectrograms can be combined additively to display how the signal power of the total acceleration and rotational rates are distributed across time and frequency. According to an alternative embodiment, the three axes are combined before calculation of a spectrogram or any other analysis of the type. The RMS of the three gyroscope channels and RMS of the three accelerometer signals are processed in order to analyze the total rotational rate, regardless of the axis of rotation and the total translational acceleration rate. This approach effectively filters out the gravitational effect because it has an average magnitude of 1, since people move in an Earth reference frame. A plurality of metrics can be calculated for each subject recordings. The accelerometer signals can be first differenced to reduce the influence of the gravitational component. This step can also be accomplished by means of a highpass filter with a specific cutoff frequency in order to avoid the amplification of high-frequency noise.

Metrics include "gross activity" detected by the accelerometers and gyroscopes. This can be quantified by lowpass filtering the corresponding power signals with a rate filter. A "tremor ratio" metric can be defined as the proportion of spectral power between 5-7 Hz relative to the total spectral power between 0.5-10 Hz. A "regularity" metric can be calculated as 1-$\gamma$ where $\gamma$ is called the spectral flatness measure. Controls should have low regularity measures when their wrists are stationary and high regularity measures when doing a repetitious activity such as the supination-pronation and tapping tasks included in this protocol. Tremor is a rhythmic activity that should increase the degree of regularity. Dyskinesia should decrease the regularity. Regularity can be computed by other means including eigenvalue spread and metrics such as Lempel-Ziv complexity, Approximate Entropy, Sample Entry, Multi-Scale entroy, as wells as other nonlinear and complexity metrics.

According to another embodiment the method or device includes plurality triaxial kinematic sensors. According to another embodiment the method and device are designed to continuously monitor and generate impairment indices for other movement disorders characterized by specific power spectral densities. The signals obtained from sensors in the device may be combined to estimate the orientation or position of the device over time. The metrics can then be computed directly from the estimates of orientation and position using state-space methods such as the Kalman filter and produce a description of the orientation in a standard format of either Euler angles or quaternions.

According to another embodiment the device and method is used to create a complete system that comprises: 1) devices to acquire and log inertial data from a plurality of sensors, 2) methods to automatically analyze raw data collected from inertial sensors in order to produce useful impairment indices, and 3) a web interface and server to collect the clinical and device data, analyze it based on methods for automatic analysis, and distribute the results to end-users.

According to one embodiment, the method is implemented in an apparatus for generating a plurality of movement impairment indices from one or more kinematic signals to characterize movement disorders, comprising: (a) one or more kinematic sensors to collect said kinematic signals; (b) means for processing said kinematic signals to reject artifacts and noise resulting in enhanced kinematic signals according to the method steps described above; (c) means finding a measure of power spectral density of said enhanced kinematic signals according to the method steps described above; (e) means for calculating a plurality of impairment indices from said measure of power spectral density according to the method steps described above; and (e) means for displaying said plurality of impairment indices using an standard display.

While particular embodiments have been described, it is understood that, after learning the teachings contained in this disclosure, modifications and generalizations will be apparent to those skilled in the art without departing from the spirit of the disclosed embodiments.

A. Example of Operation and Test Results for a Disclosed Embodiment

This section illustrates the operation and the experimentation results obtained for a specific embodiment. The embodiment, resulting plots, and results are meant simply to illustrate the disclosed embodiment the should not be interpreted as a limitations.

An example of operation and the experimentation results of one embodiment are described below. Additionally, we briefly describe the experimental methodology.

A.1. Methodology

The subjects were seated for the entire duration of the protocol. Each task lasted for 30 s. No practice was allowed, but the recording did not begin for the supination-pronation or fast-tapping tasks until the subject had started the task in a comfortable rhythm.

A time-frequency analysis (spectrogram) was performed for each of the six channels of inertial data. The power spectral densities were estimated with a modified periodogram. Each 15 s segment was multiplied with a Blackman data window. Based on the orthogonality of the accelerometer and gyroscope channels, the spectrograms were combined additively to display how the signal power of the total acceleration and rotational rates were distributed across time and frequency.

Three metrics were also calculated for each subject during each of the six tasks. The accelerometer signals were first differenced to reduce the influence of the gravitational component. This step can also be accomplish by means of a highpass filter with a specific cutoff frequency in order to avoid the amplification of high-frequency noise. The first metric measured "gross activity" detected by the accelerometers and gyroscopes. This was quantified by lowpass filtering the corresponding power signals with a rate filter. Second, the "tremor ratio" was defined as the proportion of spectral power between 5-7 Hz relative to the total spectral power between 0.5-10 Hz. Finally, a "regularity" measure was calculated as 1-$\gamma$ where $\gamma$ is called the spectral flatness measure. Controls should have low regularity measures when their wrists are stationary and high regularity measures when doing a repetitious activity such as the supination-pronation and tapping tasks included in this protocol. Tremor is a rhythmic activity that should increase the degree of regularity. Dyskinesia should decrease the regularity. Regularity can be computed by other means including eigenvalue spread and metrics such as Lempel-Ziv complexity, Approximate Entropy, Sample Entry, Multi-Scale entroy, as wells as other nonlinear and complexity metrics.

A.1. Sample Results

FIGS. 2-4 show examples of the power spectral densities during each of the six tasks for a control subject FIG. 2, a patient with tremor FIG. 3, and a patient with dyskinesia FIG. 4. The patient with tremor had clear activity at 5-6 Hz. The patient with dyskinesia had excessive and uncoordinated activity throughout the study session. Overall, the patient group had significantly higher activity metrics using both the accelerometers ($p=0.01$, 0.01) and gyroscopes ($p=0.019$, 0.038) during the mental tasks than the controls. They also had more regular activity during these tasks. Two of the patients with tremor had much higher tremor ratios during the tasks in which the subjects were trying to hold their arms still (tasks 1-2, 5-6). These results demonstrate the potential of using inertial sensors for clinical assessment of PD.

FIG. 5 shows an example of a continuous assessment of inertial sensor data collected from a male subject with PD who participated in an ongoing overnight laboratory study. Medication was withheld overnight and a levodopa infusion was given at approximately 9:00 AM the following morning. The inertial device was placed on his right wrist, which was also his most affected side. The spectrograms were calculated with a segment duration of 5 min. This figure illustrates an example of operation according to one embodiment showing analysis results obtained using the disclose embodiment described herein using inertial data from an inpatient study.

The top figure shows a spectrogram (time-frequency analysis) over a 0-10 Hz range of combined activity recorded from the accelerometers, the next figure shows the annotated activities, the middle figure shows a spectrogram of combined activity from the gyroscopes, and the bottom three plots show continuous measures of tremor, dyskinesia, and bradykinesia calculated from the inertial sensor data. The dots in the bottom figure show the average tapping interval during a 60 s tap test. Annotations include a levodopa infusion, pinch grip, tapping, standing quietly, standing with mental task, and synchronization tap.

The combined spectrograms from the accelerometers and gyroscopes show clear signs of tremor before levodopa and several hours after the levodopa infusion. Excessive activity in the 1-3 Hz frequency range shows dyskinetic activity. The bottom three plots show the relative magnitude of tremor, dyskinesia, and bradykinesia impairment indices according to one embodiment.

While particular embodiments and example results have been described, it is understood that, after learning the teachings contained in this disclosure, modifications and generalizations will be apparent to those skilled in the art without departing from the spirit of the disclosed embodiments.

The invention claimed is:

1. A method for generating a plurality of movement impairment indices from one or more kinematic signals obtained from one or more kinematic sensors, said method implemented in a digital computer with one or more processors in order to characterize movement disorders, said method comprising:
   (a) collecting said one or more kinematic signals from said one or more kinematic sensors in a wearable inertial monitoring system configured for continuous measurement of movement;
   (b) processing said one or more kinematic signals to reject artifacts and noise resulting in one or more enhanced kinematic signals;
   (c) finding a measure of power spectral density of said one or more enhanced kinematic signals; and
   (d) calculating one or more impairment indices to characterize movement disorders in Parkinson's disease or essential tremor from said measure of power spectral density.

2. The method of claim 1, further comprising detrending said one or more enhanced kinematic signals prior to finding said measure of power spectral density of said one or more enhanced kinematic signals to eliminate low frequency components of said one or more kinematic signals.

3. The method of claim 2, further comprising generating one or more total magnitude bandlimited signal powers from said one or more enhanced kinematic signals.

4. The method of claim 3, wherein said one or more total magnitude bandlimited signal powers correspond to a total magnitude of acceleration or total rotational rate within a given frequency band characterizing specific impairment conditions.

5. The method of claim 4, further comprising postprocessing said plurality of impairment indices from said measure of power spectral density to generate a plurality of smoother impairment indices for continuous quantification of tremor, dyskinesia, and bradykinesia as a function of time based on said one or more kinematic sensors.

6. The method of claim 1, wherein calculating said plurality of impairment indices from said measure of power spectral density involves computing a plurality of regularity metrics.

7. The method of claim 6, wherein said plurality of regularity metrics are chosen from the group consisting of spectral flatness, eigenvalue spread, Lempel-Ziv complexity, Approximate Entropy, Sample Entropy, Multi-Scale entropy, nonlinear metrics, and complexity metrics.

8. The method of claim 1, wherein finding said measure of power spectral density of said one or more enhanced kinematic signals includes generating a time-frequency analysis plot.

9. The method of claim 8, wherein said time-frequency analysis plot is a spectrogram showing spectral changes as a function of time.

10. The method of claim 1, wherein finding said measure of power spectral density of said one or more enhanced kinematic signals involves using a power spectral estimation method chosen from the group consisting of periodogram, modified periodogram, Barletts's method, Welch's method, Blackman-Tukey's method, autoregressive spectrum estimation, moving average spectrum estimation, autoregressive moving average spectrum estimation, and adaptive spectrum estimation.

11. The method of claim 1, wherein said one or more kinematic sensors comprise an accelerometer and a gyroscope.

12. A method for analyzing and visualizing kinematic data to characterize movement disorders, comprising:
   (a) collecting one or more kinematic signals from one or more kinematic sensors in a wearable inertial monitoring system configured for continuous measurement of movement; and
   (b) calculating and displaying a time-frequency analysis plot of said one or more kinematic signals to characterize movement disorders in Parkinson's disease or essential tremor as a function of time.

13. The method of claim 12, wherein said time-frequency analysis plot is a spectrogram showing spectral changes as a function of time.

14. An apparatus for generating a plurality of movement impairment indices from one or more kinematic signals to characterize movement disorders, comprising:
   (a) one or more kinematic sensors in an untethered wearable inertial monitoring system configured for continuous measurement of movement by collecting one or more kinematic signals; and
   (b) a processor configured for 1) processing said one or more kinematic signals to reject artifacts and noise resulting in one or more enhanced kinematic signals, 2) finding a measure of power spectral density of said one or more enhanced kinematic signals, and 3) calculating one or more impairment indices to characterize movement disorders in Parkinson's disease or essential tremor from said measure of power spectral density.

* * * * *